(12) United States Patent
Sandri et al.

(10) Patent No.: US 11,801,328 B2
(45) Date of Patent: Oct. 31, 2023

(54) ELECTROSPUN NANOFIBERS AND MEMBRANE

(71) Applicant: UNIVERSITA' DEGLI STUDI DI PAVIA, Pavia (IT)

(72) Inventors: Giuseppina Sandri, Garlasco (IT); Maria Cristina Bonferoni, Pavia (IT); Silvia Rossi, San Martino Siccomario (IT); Franca Ferrari, Pavia (IT)

(73) Assignee: UNIVERSITÁ DEGLI STUDI DI PAVIA, Pavia (IT)

( * ) Notice: Subject to any disclaimer, the term of this patent is extended or adjusted under 35 U.S.C. 154(b) by 786 days.

(21) Appl. No.: 16/633,507

(22) PCT Filed: Jul. 28, 2017

(86) PCT No.: PCT/IT2017/000160
§ 371 (c)(1),
(2) Date: Jan. 23, 2020

(87) PCT Pub. No.: WO2019/021325
PCT Pub. Date: Jan. 31, 2019

(65) Prior Publication Data
US 2020/0230290 A1    Jul. 23, 2020

(51) Int. Cl.
*A61L 27/26*   (2006.01)
*D01D 5/00*    (2006.01)

(52) U.S. Cl.
CPC .............. *A61L 27/26* (2013.01); *D01D 5/003* (2013.01); *A61L 2400/12* (2013.01); *A61L 2430/00* (2013.01)

(58) Field of Classification Search
CPC ........ A61K 9/7007; A61K 8/65; A61K 8/731; A61K 8/735; A61K 8/736; A61K 8/8147; D01D 5/0038; D01D 5/003; D01F 2/24; A61L 2400/12; A61L 27/26; A61L 2430/00
See application file for complete search history.

(56) References Cited

U.S. PATENT DOCUMENTS

| | | | |
|---|---|---|---|
| 2010/0080993 A1* | 4/2010 | Privitera | ................. D01F 1/103 428/401 |
| 2010/0254961 A1* | 10/2010 | Nishio | ...................... D01F 6/14 424/94.1 |

FOREIGN PATENT DOCUMENTS

| | | | | |
|---|---|---|---|---|
| CN | 104762753 | * | 7/2015 | |
| EP | 2 292 309 A1 | | 3/2011 | |
| EP | 2292309 | * | 9/2011 | ............. B01D 39/16 |
| EP | 2 394 670 A1 | | 12/2011 | |
| JP | 5600005 | * | 10/2014 | ........... A61K 9/7007 |
| WO | 2009/011944 A2 | | 1/2009 | |

OTHER PUBLICATIONS

Tsai (Journal of Taiwan Institute of Chemical Engineers xxx (2013) pp. 1-7, IDS) (Year: 2013).*
Ebrahimi-Hosseinzadeh et al. (Fibers and Polymers, 2016, Vo. 17, No. 6, pp. 820-826, IDS) (Year: 2016).*
Guo, Junxia et al. "Characterization and application of chondroitin sulfate/polyvinyl alcohol nanofibres prepared by electrospinning". Carbohydrate Polymers, vol. 143, pp. 239-245, 2016.
Ebrahimi-Hosseinzadeh, Bahman et al. "In vivo Evaluation of Gelatin/Hyaluronic Acid Nanofiber as Burn-wound Healing and Its Comparison with ChitoHeal Gel". Fibers and Polymers, vol. 17, No. 6, pp. 820-826, 2016.
Apr. 20, 2018 International Search Report filed in International Patent Application No. PCT/IT2017/000160.
Apr. 20, 2018 Written Opinion issued in International Patent Application No. PCT/IT2017/000160.
Nov. 28, 2019 International Preliminary Report on Patentability issued in International Patent Application No. PCT/IT2017/000160.
Ahire, J. J. et al. "Polyethylene oxide (PEO)-hyaluronic acid (HA) nanofibers with kanamycin inhibits the growth of Listeria monocytogenes". Biomedicine & Pharmacotherapy, vol. 86, pp. 143-148, 2017.
Ajalloueian, Fatemeh et al. "Emulsion Electrospinning as an Approach to Fabricate PLGA/Chitosan Nanofibers for Biomedical Applications". BioMed Research International, vol. 2014, pp. 1-13, 2014.
Alhosseini, Sanaz Naghavi et al. "Synthesis and characterization of electrospun polyvinyl alcohol nanofibrous scaffolds modified by blending with chitosan for neural tissue engineering". International Journal of Nanomedicine, vol. 2012, No. 7, pp. 25-34, 2012.
De Vrieze, Sander et al. "Electrospinning of chitosan nanofibrous structures: feasibility study". Journal of Materials Science, vol. 42, pp. 8029-8034, 2007.
Deepthi, S. et al. "Chitosan-hyaluronic acid hydrogel coated poly(caprolactone) multiscale bilayer scaffold for ligament regeneration". Chemical Engineering Journal, vol. 260, pp. 478-485, 2015.
Du, Jian et al. "Comparative evaluation of Chitosan, Cellulose Acetate, and Polyethersulfone Nanofiber Scaffolds for Neural Differentiation". Manuscript for Carbohydrate Polymers, pp. 1-27, Accepted 2013.
Figueira, Daniela R. et al. "Production and characterization of Polycaprolactone-Hyaluronic acid/Chitosan-Zein electrospun bilayer nanofibrous membrane for tissue regeneration". Manuscript for International Journal of Biological Macromolecules, pp. 1-36, Accepted 2016.
Geng, Xinying et al. "Electrospinning of chitosan dissolved in concentrated acetic acid solution". Biomaterials, vol. 26, pp. 5427-5432, 2005.
Pezeshki-Modaress, Mohamad et al. "Gelatin/Chondroitin Sulfate Nanofibrous Scaffolds for Stimulation of Wound Healing: In-Vitro and In-Vivo Study". Journal of Biomedical Materials Research: Part A, vol. 105, No. 7, pp. 1-45, Accepted 2016.
Haider, Sajjad et al. "Preparation of the Chitosan Containing Nanofibers by Electrospinning Chitosan-Gelatin Complexes". Polymer Engineering and Science, vol. 50, pp. 1887-1893, 2010.

(Continued)

*Primary Examiner* — Anna R Falkowitz
(74) *Attorney, Agent, or Firm* — Oliff PLC

(57) ABSTRACT

The present invention relates to a process for preparing nanofibers and nanofiber membranes and to the nanofibers and nanofiber membranes obtainable by such process.

11 Claims, 2 Drawing Sheets

(56) References Cited

OTHER PUBLICATIONS

Figure 1:
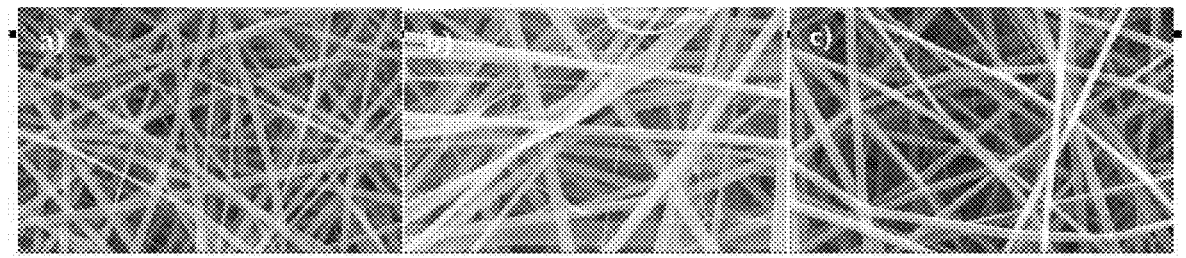

Jing, Xin et al. "Electrospun aligned poly(propylene carbonate) microfibers with chitosan nanofibers as tissue engineering scaffolds". Carbohydrate Polymers, vol. 117, pp. 941-949, 2015.

Li, Wei et al. "Preparation, Characterization, and Property of Chitosan/Polyethylene Oxide Electrospun Nanofibrous Membrane for Controlled Drug Release". Integrated Ferroelectrics, vol. 151, pp. 164-178, 2014.

Lin, Chi-Chang et al. "Chitosan-coated electrospun PLA fibers for rapid mineralization of calcium phosphate". Manuscript for International Journal of Biological Macromolecules, pp. 1-39, Accepted 2014.

Pezeshki-Modaress, Mohamad et al. "Fabrication of Gelatin/Chitosan Nanofibrous Scaffold: Process Optimization and Empirical Modeling". pp. 1-25, 2013.

Pezeshki-Modaress, Mohamad et al. "Gelatin-GAG electrospun nanofibrous scaffold for skin tissue engineering: Fabrication and modeling of process parameters". Materials Science and Engineering C, vol. 48, pp. 704-712, 2015.

Savoji, Houman et al. "Combining Electrospun Fiber Mats and Bioactive Coatings for Vascular Graft Prostheses". Biomacromolecules, vol. 18, No. 1, pp. 303-310, 2017.

Shahzad, Sohail et al. "Chitosan-based electrospun nanofibrous mats, hydrogels and cast films: novel anti-bacterial wound dressing matrices". Journal of Materials Science: Materials in Medicine, vol. 26, No. 136, pp. 1-12, 2015.

Shin, Yong Cheol et al. "Hyaluronic Acid/PLGA Core/Shell Fiber Matrices Loaded with EGCG Beneficial to Diabetic Wound Healing". Advanced Healthcare Materials, vol. 5, pp. 3035-3045, 2016.

Tsai, Reui-Yi et al. "Electrospun chitosan-gelatin-polyvinyl alcohol hybrid nanofibrous mats: Production and characterization". Journal of the Taiwan Institute of Chemical Engineers, pp. 1-7, 2013.

Vondran, Jennifer L. et al. "Crosslinked, Electrospun Chitosan-Poly(ethylene oxide) Nanofiber Mats". Journal of Applied Polymer Science, vol. 109, pp. 968-975, 2008.

Xu, Fenghua et al. "Development of tannic acid/chitosan/pullulan composite nanofibers from aqueous solution for potential applications as wound dressing". Carbohydrate Polymers, vol. 115, pp. 16-24, 2015.

\* cited by examiner

ELECTROSPUN NANOFIBERS AND MEMBRANE

The present invention relates to electrospun glycosaminoglycan-containing nanofibers and membranes formed of said nanofibers, to processes for producing said nanofibers and membranes, as well as uses thereof for promoting cutaneous wound healing of chronic lesions and burns and for the treatment of ischemic cardiac tissue caused by acute infarction.

Nanofibers are fibers with diameters in the nanometer range. Nanofibers can be generated from different polymers and hence have different physical properties and application potentials. Examples of natural polymers include collagen, silk fibroin, keratin, gelatin and polysaccharides such as cellulose, chitosan and alginate.

It is known that nanofibers based membranes have shown positive results as scaffolds to enhance cell adhesion and proliferation.

Electrospinning is the most commonly used method to fabricate nanofibers. According to this simple and versatile technique, an electrical field is applied between a needle and a collector surface, generally made of a metallic plate. A polymer solution is fluxed from a syringe through said needle tip and the applied electric field causes a deformation of the polymer solution fluid from a spherical pendant drop to a cone, called Taylor cone. A critical value of electrical field is requested to surpass a threshold value at which the electrostatic repulsion force, due to charges located at drop surface, overcomes surface tension. This results in the ejection from the tip of the Taylor cone of a charged fluid jet and in deposition thereof on the collector. The electrospinning process allows the deposition of ultrafine and long nanofibers, as well as formation of a non-woven structure. However, if the fluid jet is unstable, due to charge interaction with the external electrical field and solvent evaporation, bending and spraying occur, thus jeopardizing the formation of fibers of suitable morphology.

Besides charge density and applied voltage, other parameters that influence the final nanofiber structure are polymer type and concentration, type of solvent, presence of electrolyte, type and concentration of electrolyte, viscosity, surface tension, tip-to collector distance, polymer solution flow, inner tip diameter.

It is known that glycosaminoglycans (GAGs) play a crucial role in different stages of skin tissue regeneration and maturation, being an important component of its extracellular matrix (ECM). Moreover glycosaminoglycans are able to bind proteins including several chemokines and growth factors. The polysaccharidic backbone of glycosaminoglycans as well as the presence, position and number of sulfate groups within the polymer chain plays an important role on these GAG-protein interactions. Among glycosaminoglycans, hyaluronic acid and chondroitin sulfate are soluble in aqueous environment. For this reason in order to prepare scaffolds containing GAGs, it is necessary to operate a chemical modification thereof, or to graft them with other polymers to decrease the solubility in aqueous environment, or to use an association with water-insoluble polymers.

For example, Biomacromolecules 2017 18 (1), 303-310 "Combining Electrospun Fiber Mats and Bioactive Coatings for Vascular Graft Prostheses" H. Savoji, et al, discloses grafting of chondroitin sulfate by carbodiimide chemistry to polyethylene terephthalate fibers after an electrospinning process.

J Biomed Mater Res Part A 2017:105A:2020-2034 "Gelatin/chondroitin sulfate nanofibrous scaffolds for stimulation of wound healing: In-vitro and in-vivo study" Pezeshki-Modaress M, et al. discloses gelatin/chondroitin sulfate scaffolds prepared by electrospinning a polymeric solution in trifluoroethanol and water 50:50 and by crosslinking the fibers in a subsequent step by adding 0.02 g N-(3-dimethylaminopropyl)-N'-ethylcarbodiimide hydrochloride.

Carbohydrate Polymers, Volume 143, 5 Jun. 2016, Pages 239-245 "Characterization and application of chondroitin sulfate/polyvinylalcohol nanofibres prepared by electrospinning" J. Guo, et al, discloses composite nanofibers prepared by electrospinning from a solution of chondroitin sulfate and polyvinyl alcohol and subsequent crosslinking with glutaric aldehyde.

Recently, hyaluronic acid was associated to PLGA in Advanced Healthcare Materials 5(23), pp. 3035-3045 (2016); "Hyaluronic Acid/PLGA Core/Shell Fiber Matrices Loaded with EGCG Beneficial to Diabetic Wound Healing" Shin, Y. C. et al; it was associated to PEO in Biomedicine and Pharmacotherapy 86, pp. 143-148 (2017) "Polyethylene oxide (PEO)-hyaluronic acid (HA) nanofibers with kanamycin inhibits the growth of *Listeria monocytogenes*" Ahire, J. J., et al; and to poly-ε-caprolactone in International Journal of Biological Macromolecules 93, pp. 1100-1110 (2016) "Production and characterization of polycaprolactone-hyaluronic acid/chitosan-zein electrospun bilayer nanofibrous membrane for tissue regeneration".

Fibers Polym (2016) 17: 820-6 "In vivo evaluation of gelatin/hyaluronic acid nanofiber as Burn-wound healing and its comparison with ChitoHeal gel", Ebrahimi-Hosseinzadeh, B. et al, discloses a process comprising electrospinning of hyaluronic acid and gelatin and subsequent crosslinking in presence of glutaraldehyde.

It is also known that chitosan, a partially N-deacetylated product of chitin, the second most abundant natural polysaccharide, has many useful properties such as biocompatibility, biodegradability, antimicrobial activity, and wound healing properties.

However, it is also known that pure chitosan is hardly spinnable, pure chitosan fibers being obtained only under very specific conditions.

For example, electrospinning of chitosan nanofibers from aqueous chitosan solution using concentrated acetic acid solution has also been described in X. Geng, O.-H. Kwon, J. Jang, "Electrospinning of chitosan dissolved in concentrated acetic acid solution", Biomaterials 26 (2005) 5427-5432. However, this publication discloses that only chitosan of a molecular weight of 106,000 g/mol produced bead-free, uniform chitosan nanofibers, while low- or high-molecular weight chitosane of 30,000 and 398,000 g/mol resulted in fibers with inconsistent morphology such as droplet and fiber or fibers with spindle-like beads.

S. De Vrieze, P. Westbroek, T. Van Camp, L. Van Langenhove, Electrospinning of chitosan nanofibrous structures: feasibility study J Mater Sci (2007) 42:8029-8034 describes that an accurate selection of various process parameters is necessary in order to obtain deposition of chitosan nanofibers. In particular, a very high concentration of acetic acid is necessary. In addition this publication discloses that, even under the prescribed conditions, the jet of the chitosan solution remains stable only for a limited time.

Typically, blends of chitosan with another polymer, such as polyethylene oxide) (PEO) or poly(vinyl alcohol) (PVA), have been used for the production of electrospun membranes.

Electrospinning of chitosan solutions associated with semisynthetic or synthetic spinnable polymers in water/ organic solvent mixture has been described, for example, in Jing X., Mi H.-Y., Peng J., Peng X.-F., Turng L.-S., "Electrospun aligned polypropylene carbonate) microfibers with chitosan nanofibers as tissue engineering scaffolds", 2015, Carbohydrate Polymers, 117 941-949; "Chitosan-hyaluronic acid hydrogel coated poly(caprolactone) multiscale bilayer scaffold for ligament regeneration", 2015, Chemical Engineering Journal, 260 478-485; Pezeshki-Modaress M., Zandi M., Mirzadeh H., "Fabrication of gelatin/chitosan nanofibrous scaffold: Process optimization and empirical modeling", 2015, Polymer International, 64 571-580; Shahzad S., Yar M., Siddiqi S. A., Mahmood N., Rauf A., Qureshi Z.-U.-A., Anwar M. S., Afzaal S., "Chitosan-based electrospun nanofibrous mats, hydrogels and cast films: novel anti-bacterial wound dressing matrices", 2015, Journal of Materials Science: Materials in Medicine, 26 1-12; Li W., Luo T., Shi Y., Yang Y., Huang X., Xing K., Liu L., Wang M., "Preparation, characterization, and property of chitosan/polyethylene oxide electrospun nanofibrous membrane for controlled drug release", 2014, Integrated Ferroelectrics, 151 164-178; Ajalloueian F., Tavanai H., Hilbom J., Donzel-Gargand O., Leifer K., Wickham A., Arpanaei A., "Emulsion electrospinning as an approach to fabricate PLGA/chitosan nanofibers for biomedical applications", 2014, BioMed Research International, 2014, 475280; Tsai R.-Y., Hung S.-C., Lai J.-Y., Wang D.-M., Hsieh H.-J., "Electrospun chitosan-gelatin-polyvinyl alcohol hybrid nanofibrous mats: Production and characterization", 2014, Journal of the Taiwan Institute of Chemical Engineers, 45, 4, 1975, 1981; Du J., Tan E., Kim H. J., Zhang A., Bhattacharya R., Yarema K. J., "Comparative evaluation of chitosan, cellulose acetate, and polyethersulfone nanofiber scaffolds for neural differentiation", 2014, Carbohydrate Polymers, 99, 483, 490; Lin C.-C., Fu S.-J., Lin Y.-C., Yang I.-K., Gu Y., "Chitosan-coated electrospun PLA fibers for rapid mineralization of calcium phosphate", 2014, International Journal of Biological Macromolecules, 68, 39, 47; Alhosseini S. N., Mortarzadeh F., Mozafari M., Asgari S., Dodel M., Samadikuchaksaraei A., Kargozar S., Jalali N., "Synthesis and characterization of electrospun polyvinyl alcohol nanofibrous scaffolds modified by blending with chitosan for neural tissue engineering", 2012, International Journal of Nanomedicine, 7, 25, 34, Haider S., Al-Masry W. A., Bukhari N., Javid M., "Preparation of the chitosan containing nanofibers by electrospinning chitosan-gelatin complexes", 2010, Polymer Engineering and Science, 50, 9, 1887, 1893, Vondran J. L., Sun W., Schauer C. L., "Cross-linked, electrospun chitosan-poly(ethylene oxide) nanofiber mats", 2008, Journal of Applied Polymer Science, 109, 2, 968, 975.

CN103705969 describes a method for preparing a chitosan-based silver-loaded composite antimicrobial superfine fiber membrane comprising polyoxyethylene or polyvinyl alcohol.

WO2011151225 discloses layered chitosan biomimetic scaffolds comprising at least two fused layers, wherein at least one of the fused layers comprises a chitosane nanofiber membrane and the other fused layer comprises a porous chitosan support layer. This document describes the preparation of the chitosan nanofiber membrane by eletrospinning a solution of chitosan with a polymer such as polyethylene oxide (PEO) to improve its spinnability.

However, the so produced nanofibers and membranes contain chitosan associated with synthetic polymers could be not completely biodegradable and/or biocompatible. In addition, the nanofibers and membranes obtained by the above mentioned methods could also contain residues of toxic organic solvents and surfactants.

Fibers and membranes containing chitosan were obtained, according to the prior art, also by means of techniques other than electrospinning, such as Forcespinning®. As opposed to eletrospinning, Forcespinning® utilizes centrifugal forces and high temperatures to prepare molded and spun polymeric fibers. Relevant parameters in this technique are spinneret angular velocity and orifice radius, polymer viscoelasticity (which includes viscosity and relaxation time of the material), surface tension, evaporation rate (for solvent in solution) and temperature (melting and solidification), and distance of spinneret orifice to collector.

Xu F., Wenga B., Gilkerson R., Materon L. A., Lozano K., "Development of tannic acid/chitosan/pullulan composite nanofibers from aqueous solution for potential applications as wound dressing" Carbohydrate Polymers 115 (2015) 16-24, describes biocompatible tannic acid/chitosan/pullulan nanofibers developed, starting from a solution comprising 18 wt % pullulan and 3% wt % chitosan/citric acid salt, using the Forcespinnig® technique. In the described method, chitosan is blended with a high amount of pullulan.

JPH01221506 discloses a method for obtaining extremely fine fibers of organic polymers such as alginate collagen, polyvinyl alcohol, pullulan, chitosan, gelatin or 'konjak' mannan, by delivering through a nozzle a solution of the organic polymer along with a gas and by bringing said flow into contact with a coagulating solution.

However, electrospinning of such organic polymers for obtaining fibers or membranes is not mentioned.

CN104307026 discloses a hemostatic dressing that contains, by weight, 8-20 parts of pullulan, 10-25 parts of chitosan glutamate, 28-40 parts of carboxymethyl chitin, 20-38 parts of glucan, 8-15 parts of sodium hyaluronate, 3-8 parts of indigo naturalis, 3-8 parts of an antibacterial agent, 3-8 parts of an anti-inflammatory agent and 10-18 parts of a plasticizer. The dressing provided by the invention is suitable for medical purposes such as rapid haemostasis, antibiosis, antiphlogosis and wound healing promotion.

However, electrospinning of such substances for obtaining fibers or membranes is not mentioned.

Gelatin is a natural biopolymer derived from collagens by controlled hydrolysis. There are generally two types of gelatin: Type A and Type B. Gelatin Type A is extracted and processed by acidic pretreatment from collagens, whereas gelatin Type B is obtained by alkaline pretreatment. The alkaline pretreatment converts glutamine and asparagine residues into glutamic and aspartic acid, which leads to higher carboxylic acid content for gelatin Type B than for gelatin Type A. Gelatin is characterized by biodegradability, biocompatibility, and commercial availability at relatively low cost and it is widely used in pharmaceutical and medical fields, in particular as sealants for vascular prostheses, dressings for wound healing. As aqueous solution gelatin is characterized by a sol-gel transition at 37° C.: at low temperature it is hydrogel, while at higher temperature it is a solution and for these reason it is rarely considered as a candidate material for tissue engineering applications without any special treatment (e.g., cross-linking). Nevertheless, the approach of mixing gelatin with other (synthetic) polymers or the chemical cross-linking are feasible approach that may not only reduce the potential problem of cytotoxicity.

Materials Science and Engineering C, 48, 704-712, 2015 "Gelatin-GAG electrospun nanofibrous scaffold for skin tissue engineering: Fabrication and modeling of process parameters" Pezeshki-Modaress M. et al, discloses a process wherein a homogeneous solution containing gelatin and chondroitin sulfate in a mixture of trifluoroethanol (TFE) and water is subjected to electrospinning to form fibers that are subsequently crosslinked by using 1-ethyl-3-3-dimethylaminopropylcarbodiimide hydrochloride.

The object of the present invention is to provide a largely practicable, one-pot process for producing water-insoluble electrospun nanofibers and membranes containing glycosaminoglycans, that are free from organic solvents and suitable for wound healing and for supporting cell growth.

Another object is to provide a method for producing chitosan based nanofibers and membranes containing glycosaminoglycans, by electrospinning, starting from chitosan of any molecular weight.

In a first aspect thereof, the present invention relates to a process for the preparation of glycosaminoglycan-containing nanofibers according to claim 1.

A first advantage of the process according to the present invention is that it employs the simple electrospinning technique, allowing a one-step production of ultrafine and long fibers as a non-woven structure.

Another advantage of the process according to the invention consists in that water is employed as the only solvent.

In an additional aspect thereof, the present invention relates to a process according to claim 7, which by a further crosslinking step allows the production of a glycosaminoglycan-containing nanofiber membrane.

In a further aspect thereof, the present invention relates to a glycosaminoglycan-containing nanofiber or a glycosaminoglycan-containing nanofiber membrane obtained by the above mentioned processes.

In another aspect, the present invention also relates to a glycosaminoglycan-containing nanofiber membrane for use as a wound dressing or scaffold, for example in patients with chronic, poorly-healing wounds, such as diabetic foot, decubitus (ulcers) or wounds due to venous or arterial insufficiency, in tissue engineering or for biomedical applications as treatment of acute myocardial infarction.

Further advantages and features of the according to the present invention will become clear to those skilled in the art from the following detailed and non-limiting description of embodiments thereof.

The process for the preparation of nanofibers according to said first aspect of the present invention, comprises the following steps:
a) providing a water solution containing:
  at least a glycosaminoglycan in an amount from 0.01% to 5.00%;
  at least a polymer chosen selected in the group consisting of polysaccharides and gelatins, in amount of 1% to 30%
  acetic acid in amount of at least 20%; and
  a polycarboxylic acid in an amount of 0.10% to 5.00%;
  all percentages being by weight with respect to the total weight of the water solution; and
b) electrospinning said water solution on a collector of an electrospinning apparatus to form nanofibers.

The water solution provided in step a) preferably comprises no organic solvents.

The glycosaminoglycans used in the water solution of step a) are preferably selected in the group consisting of chondroitin sulfate, hyaluronic acid, and mixtures thereof.

Said glycosaminoglycans may be preferably comprised in the water solution provided in step a) in an amount of between 0.10% and 1.00%; preferably in an amount of 0.5%±0.1%, by weight with respect to the total weight of the solution.

In an embodiment of the present invention, said water solution provided in step a) comprises chondroitin sulfate in an amount of 0.01% to 5%; preferably in an amount of 0.10 to 1.00%; or in amount of 0.5%±0.1%, all percentages being by weight with respect to the total weight of the solution.

In another embodiment said glycosaminoglycans are in an amount of 0.5±0.05%, percentages being by weight with respect to the total weight of the water solution.

The polysaccharides that may be used in the water solution according to the present invention may be selected in the group consisting of hydrophilic cellulose derivatives, in particular carboxymethylcellulose; alginate; pullulan; mixtures of pullulan and chitosan; and mixtures of pullulan and carboxymethylcellulose.

In a first embodiment of the present invention said polymer is a mixture of polysaccharides and in particular a mixture of pullulan and chitosan. Said mixture preferably comprises chitosan in amount of 1% to 4% and pullulan in amount of 7% to 15%, wherein all percentages being by weight with respect to the total weight of the water solution. Chitosan and pullulan are usually added in a mixture of water and acetic acid, by gentle stirring at room temperature, to obtain the water solution intended to be electrospun in step b).

In another embodiment, the mixture of chitosan and pullulan may comprise chitosan in amount between 2% and 3% w/w and pullulan in amount between 8% and 12% w/w.

In another embodiment, solutions comprising chitosan in amount of 2.5%±0.1% w/w; and pullulan in amount of 10%±0.1 w/w % may be provided.

The water solutions of step a) may be prepared by dissolving under stirring the appropriate amount of chitosan and pullulan in an acetic acid solution of minimum concentration 20% w/w of acetic acid.

In an embodiment, said polymer is gelatin type B in an amount of 10 to 30%, preferably of 15% to 25% w/w, with respect to the total weight of the water solution.

In an advantageous embodiment, the concentration of acetic acid in the water solution provided in step a) according to the present invention is at least 35%, or at least 40%, or 45%±1% w/w with respect to the weight of the water solution.

In order to perform the crosslinking step, the water solution provided in step a) also comprises a polycarboxylic acid in amount of 0.1% to 5% w/w, or in amount of 2% to 3% w/w, wherein percentages are by weight with respect to the total weight of the solution.

Useable polycarboxylic acids are, for example: citric acid, glutamic acid or mixtures thereof.

According to an embodiment of the process according to the invention, said water solution provided in step a) comprises citric acid.

In step (b) the so provided water solution is electrospun, using an electrical charge to draw very fine (typically on the micro or nano scale) fibers, by a known process as already mentioned in the introductory part of the present application. A standard electrospinning apparatus consists of a spinneret (typically a hypodermic syringe needle) connected to a high-voltage (in general 5 to 50 kV) direct current power supply, a syringe pump, and a grounded collector.

The water solution provided in step a) is thus fed in an injector of an electrospinning apparatus, such as a syringe. By applying an electrospinning voltage between said injector and the collector of the electrospinning apparatus, nanofibers are deposited onto said collector. The preparation process may be performed at room temperature.

The process for the preparation of electrospun nanofibers may be performed by applying an electrospinning voltage between 15 and 30±1 kV. In some embodiments, the electrospinning voltage is 15, 20, 22, 25 and 30±1 kV.

Further, the process for the preparation of electrospun nanofibers may be performed with an electrospinning apparatus wherein the distance between the tip of the spinneret and the collector is between 15 and 30±1 cm, or between 15 and 20 cm. In some embodiments, said distance is 15, 20, 25, and 30 cm.

The flux of the water solution provided in step a) through the spinneret may be between 0.1 ml/h and 2.0 ml/h. In an embodiment of the present invention, said flux is between 0.3 and 1.6 ml/h, or between 0.7 and 1.2 ml/h. In some embodiments, said flux is 0.397 ml/h; 0.793 ml/h; 0.8 ml/h; 1.19 ml/h; and 1.53 ml/h.

During electrospinning, a tridimensional structure is provided by the progressive accumulation of the electrospun nanofibers. As known, the use of a movable collector could allow the guidance of the electrospun nanofibers and the development of specific nanofiber networks.

In an embodiment of the present invention, the diameter of the obtained nanofibers ranges from 200 to 1000 nm.

The layered nanofibers are then collected.

According to a further aspect thereof, the process of the present invention is usable to prepare a glycosaminoglycan-containing nanofiber membrane by means of a further step c), wherein the nanofibers obtained in step b) are crosslinked.

In the context of the present invention, the terms "membrane" or "scaffold" relate to a three-dimensional object containing pores and empty spaces that can be invaded and populated by cells or that can have various functions or properties such as, among others, absorption of wound exudates.

Said crosslinking may be carried out by heating said nanofibers at a temperature of 100° C. to 170° C. for a period of at least 15 minutes. Preferably, said crosslinking comprises heating of said nanofibers at a temperature of 150±1° C. for a period of at least 15 minutes.

The present invention also relates, in additional aspects thereof, to nanofibers and nanofiber membranes obtainable by the process according to the invention and to their use as a wound dressing, in tissue engineering or for biomedical applications.

As surprisingly found in the present application and as illustrated in the appended examples, an association of polymers having opposite charges and potentially able to form insoluble polyelectrolyte complexes (PEC), such as negatively charged glycosaminoglycans and positively charged polysaccharides or gelatin, form instead an electrospinnable mixture and allow to obtain, by means of a simple procedure, an electrospun membrane that merges the bioactive properties of all the biopolymers contained in the water solution.

Thus, the invention provides a therapeutic option to heal chronic or serious lesions and in particular skin lesions. The membranes according to the present invention may be used as skin substitute in presence of skin lesions of different origins. These membranes are suitable to be used also for mucosal application in the case of mucosal ulcers (buccal, esophageal, vaginal). Moreover scaffolds could be used as implantable systems to treat ischemic area after myocardial acute infarction.

The membranes according to the present invention show mechanical properties suitable to support cell adhesion and growth and the movement of the tissue (force at break ranging from 10 to 100 N and deformation from 10 to 100% in wet state).

The membranes according to the present invention, obtained after crosslinking step c), are insoluble in water and can act as support for cell growth inducing cell migration and cell proliferation. The membranes according to the present invention are obtained from a process that makes no use of organic solvents, thus are free of residues that could impair healing process.

The nanofibers or the membranes according to the present invention may be further loaded with antimicrobial agents by mixing polymer solution with an active ingredient and by proceeding with the previously described preparation method. This could speed up the reparation process in case of infection risks or to eliminate interfering effect on healing due to a present infection. Antimicrobial agents suitable to be loaded on the chitosan nanofibers or the membranes according to the present invention include silver nanoparticles and silver nitrate, or antibiotics such as for example norfloxacin, gentamicin, mupirocin. The antimicrobial agents to be loaded in the nanofibers or membrane according to the present invention may also be included in a clay nanocomposites or in clay complex.

Therefore, the application of these membranes on the damaged skin allows to protect the area against microbial contamination and allows gas exchange that is crucial to achieve healing.

In the following, the invention will be illustrated with reference to the subsequent examples.

EXAMPLES

The following compositions were prepared.

Composition 1:
Chitosan base (deacetylation degree 98% ChitoClear low molecular weight 251000 Da, Primex, N) 2.5% w/w;
Pullulan (food grade, Hayashibara, J) 10%.
Citric acid 2.5% w/w
All the components were dissolved in acetic acid aqueous solution at 45% w/w.

Composition 2
Chondroitin sulfate (100 EP, Bioiberica) 0.5% w/w.
Chitosan base (deacetylation degree 98% ChitoClear low molecular weight 251000 Da, Primex, N) 2.5% w/w;
Pullulan (food grade, Hayashibara, J) 10%.
Citric acid 2.5% w/w
All the components were dissolved in acetic acid aqueous solution at 45% w/w.

Composition 3
Hyaluronic sodium salt (intraocular, low molecular weight, Bioiberica) 0.5% w/w.
Chitosan base (deacetylation degree 98% ChitoClear low molecular weight 251000 Da, Primex, N) 2.5% w/w;
Pullulan (food grade, Hayashibara, J) 10%.
Citric acid 2.5% w/w
All the components were dissolved in acetic acid aqueous solution at 45% w/w.

Composition 4:
Chondroitin sulfate (100 EP, Bioiberica) 0.5% w/w.
Pullulan (food grade, Hayashibara, J) 10%.
Citric acid 2.5% w/w
All the components were dissolved in acetic acid aqueous solution at 45% w/w.

Composition 5
Hyaluronic sodium salt (intraocular, low molecular weight, Bioiberica)

Pullulan (food grade, Hayashibara, J) 10%.
Citric acid 2.5% w/w
All the components were dissolved in acetic acid aqueous solution at 45% w/w.
Composition 6:
Chondroitin sulfate (100 EP, Bioiberica) 0.5% w/w.
Gelatin B 10%.
Citric acid 2.5% w/w
All the components were dissolved in acetic acid aqueous solution at 45% w/w.
Composition 7:
Hyaluronic sodium salt (intraocular, low molecular weight, Bioiberica)
Gelatin B 10%.
Citric acid 2.5% w/w
All the components were dissolved in acetic acid aqueous solution at 37.5% or 45% w/w.

The so obtained compositions 1, 2, 3, 4 were electrospun, separately from each other, by using an eletrospinning apparatus equipped with a high voltage DC (direct current) source (40 kV), a 10 ml syringe with luer-lock connections to a metallic tip, a volumetric pump (Razel R99-E) and a Plexiglass® collector coated with aluminum foil for random collection and a rotating drum for aligned nanofibers. The so obtained nanofibers were subjected to thermal treatment at 150° C. for 1 h to obtain insoluble membranes.

In the attached figures:

FIG. 1 shows SEM (Scanning Electron Microscopy) images of nanofibrous membranes obtained from a) composition 1 b) composition 2; and c) composition 3.

Figure 2:
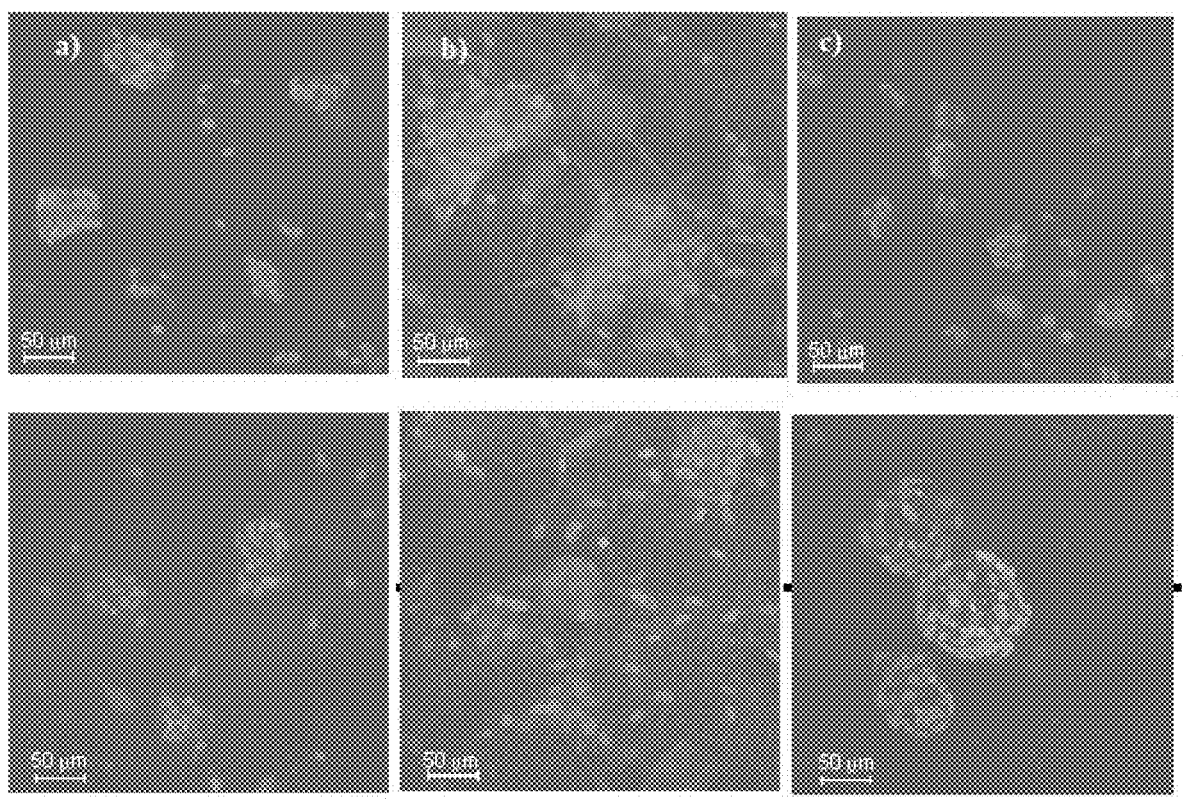
Figure 3:
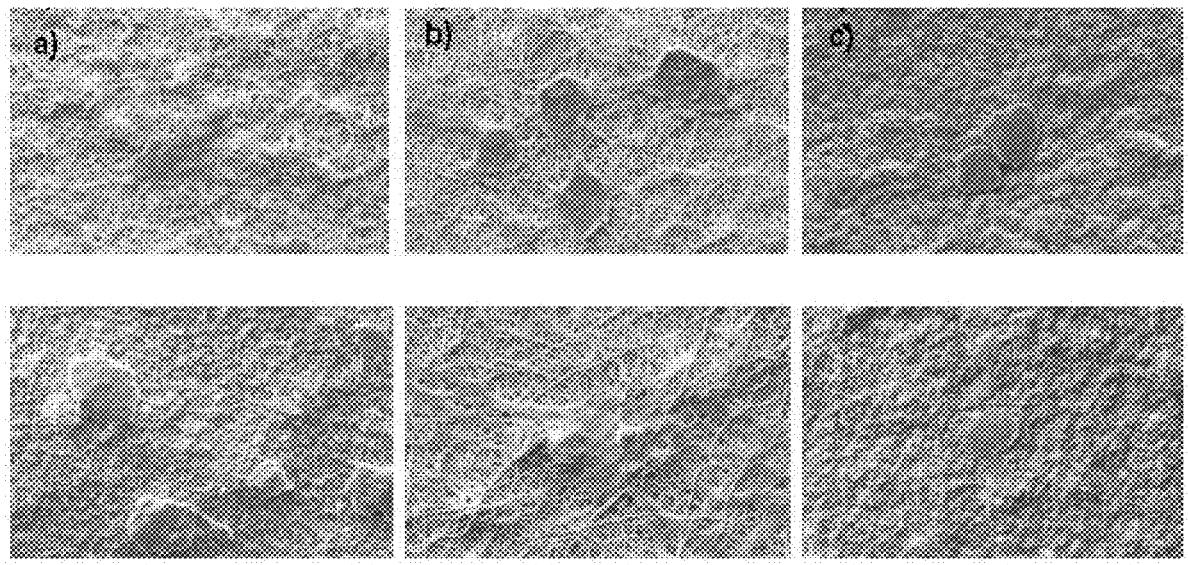
Figure 4:
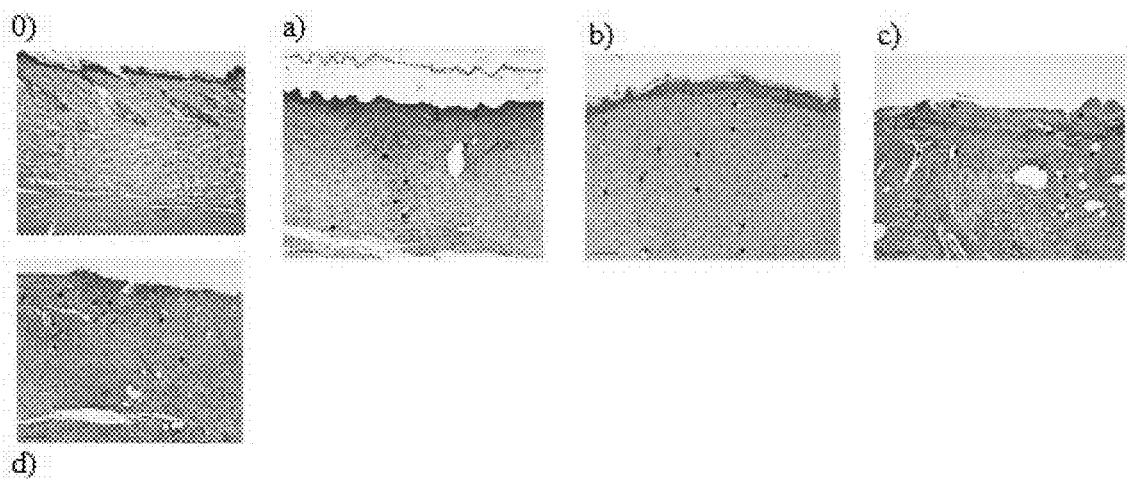

FIG. 2 shows CLSM (Confocal Laser Scanning Microscopy) images of fibroblasts grown on the membranes of FIG. 1 after 7 days of growth;

FIG. 3 shows SEM (Scanning Electron Microscopy) images of fibroblasts grown on the membranes of FIG. 1 after 7 days of growth; and FIG. 4 shows histology of intact skin section 0) and skin sections after 18 days of treatment with the membranes obtained from a) composition 1 b) composition 2; and c) composition 3 and d) saline solution as negative control.

The invention claimed is:

1. A process for the preparation of an insoluble glycosaminoglycan-containing nanofiber membrane, comprising:
 a) providing a water solution containing:
  at least a glycosaminoglycan in an amount from 0,01% to 5,00%;
  at least a polymer chosen in the group consisting of hydrophilic cellulose derivatives; pullulan; mixtures of pullulan and chitosan; mixtures of pullulan and hydrophilic cellulose derivatives; and gelatins, said polymer being in an amount of 1% to 30%;
  acetic acid in amount of at least 20%; and
  a polycarboxylic acid in an amount of 0,1% to 5,00%;
  all percentages being by weight with respect to the total weight of the water solution;
 b) electrospinning said water solution on a collector of an electrospinning apparatus to form nanofibers; and
 c) crosslinking said nanofibers to obtain the insoluble glycosaminoglycan-containing nanofiber membrane, wherein the crosslinking is performed without glutaraldehyde vapors.

2. The process according to claim 1, wherein said polymer is a mixture of chitosan in amount of 1% to 4% and pullulan in amount of 7% to 15%, all percentages being by weight with respect to the total weight of the water solution.

3. The process according to claim 1, wherein said polymer is gelatin type B in an amount of 15% to 25%, all percentages being by weight with respect to the total weight of the water solution.

4. The process according to claim 1, wherein said glycosaminoglycan is in an amount of 0.5±0.05%, percentages being by weight with respect to the total weight of the water solution.

5. The process according to claim 1, wherein said water solution further comprises antimicrobial agents.

6. The process according to claim 1, wherein said crosslinking comprises heating said nanofibers at a temperature of 100° C. to 170° C. for a period of at least 15 minutes.

7. The process according to claim 6, wherein said crosslinking comprises heating of said nanofibers at a temperature of 150±1° C. for a period of at least 15 minutes.

8. The process according to claim 1, wherein said polycarboxylic acid is citric acid or glutamic acid.

9. The process according to claim 8, wherein said water solution comprises citric acid in amount of 2% to 3%, all percentages being by weight with respect to the total weight of the solution.

10. The process according to claim 9, wherein said glycosaminoglycan is selected in the group consisting of chondroitin sulfate, hyaluronic acid and mixtures thereof.

11. The process according to claim 1, wherein the crosslinking is performed without a toxic crosslinking agent.

* * * * *